United States Patent
Johansson et al.

[11] Patent Number: 6,005,164
[45] Date of Patent: Dec. 21, 1999

[54] IMPLANT WITH POROUS SURFACE

[75] Inventors: Thomas Johansson, Hoganas; Ralph Harysson, Trollhättan; Leif Hermansson, Uppsala, all of Sweden

[73] Assignee: LuCoCer Aktiebolag, Hoganas, Sweden

[21] Appl. No.: 09/037,981

[22] Filed: Mar. 11, 1998

Related U.S. Application Data

[63] Continuation-in-part of application No. 08/619,608, Apr. 10, 1996.

[51] Int. Cl.$^6$ .............................. A61F 2/28; B08B 7/00; B44C 1/22
[52] U.S. Cl. .................. 623/16; 134/7; 156/648
[58] Field of Search .............. 623/16; 156/643; 134/7

[56] References Cited

U.S. PATENT DOCUMENTS

| | | | |
|---|---|---|---|
| 3,808,606 | 5/1974 | Tronzo | 3/1 X |
| 4,195,366 | 4/1980 | Jarcho et al. | 3/1.9 |
| 5,222,983 | 6/1993 | Schmitz et al. | 623/16 X |
| 5,246,530 | 9/1993 | Bugle et al. | 156/643 |
| 5,344,494 | 9/1994 | Davidson et al. | 134/7 |

*Primary Examiner*—Mickey Yu
*Assistant Examiner*—Hieu Phan
*Attorney, Agent, or Firm*—Nixon & Vanderhye

[57] ABSTRACT

Implant intended to be fixed through contact with new grown bone tissue comprising a dense material having an implant surface, and having, at least within a surface portion of the implant surface, surface pores covering at least 5% of the surface portion. The surface pores constitute a contact surface for new grown bone tissue, wherein close to at least a substantial fraction of all of the surface pores has at least one elevation extending over the implant surface which completely or at least partially surrounds an edge of the pore. Each elevation has a rough surface which causes formation of soft tissue when the implant surface is in contact with newly growing bone tissue.

14 Claims, 5 Drawing Sheets

0 100 200 300 μm 0 100 200 300 μm

IMPLANT WITH POROUS SURFACE

CROSS-REFERENCE TO RELATED APPLICATION

The present application is a continuation-in-part of application Ser. No 08/619,608, filed Apr. 10, 1996 (incorporated herein by reference), and still pending.

TECHNICAL FIELD

The present invention relates to implants having improved retention when fixed through contact with new grown bone tissue.

BACKGROUND OF THE INVENTION

When using supporting implants it is important that the implant material has a high strength and that a sufficiently high resistance to shearing forces is developed between the implant and new grown bone tissue. The latter feature is important for achieving good retention. High strength implant materials can be achieved by using dense materials having an inherent high strength, such as conventional construction materials, for example stainless steel, cobalt-chromium alloys, titanium and titanium alloys, ceramic materials or polymers or materials with controlled defects, including pores.

For the fixation of implants to bone, it is known in the art to utilize a topographic surface or pores. Retention is achieved through the establishment of a good contact between the implant and new grown bone tissue.

Swedish Patent No. 468 502 discloses certain aspects relating to the pore size distribution in porous implant materials. Specific and complex pore size distributions in this respect have been found possible to use for depositing bone growth promoting substances and in order to stimulate a good bone ingrowth in larger pores.

Swedish patent application No. 9200072-8 describes how the microporosity of an implant can be utilized for the deposition of one or more bone growth promoting substances by means of carriers prior to implantation. By filling the pores to a different degree with carriers having a poor solubility, and with appropriate active agents, the formation of pores for bone ingrowth and for release of active substances can be controlled in order to achieve an optimal ingrowth.

SUMMARY OF THE INVENTION

It is an object of the invention to provide an implant material having an improved retention when in contact with new grown bone tissue. This is achieved, according to the invention, by optimizing the pore sizes and by the provision of a topography of the pore brim which will enhance retention. In at least a substantial fraction of all of the surface pores there is at least one elevation which is higher than the implant surface surrounding the brim of the pore. The elevation(s) is not bound to any specific topography, but preferably has the shape of one or more ridges which partly or completely surround the pore. The implant at least partly consists of a dense material having, at least within a portion of its surface, surface pores, which cover at least 5% of the surface portion, more usually 5–40% of the surface portion, which constitutes a contact surface for new grown bone tissue.

According to one aspect of the invention, there is provided an implant intended to be fixed through contact with new grown bone tissue. The implant comprises a dense material having an implant surface and having, at least within a surface portion of the implant surface, surface pores covering at least 5% of the surface portion. The surface pores constitute a contact surface for new grown bone tissue, wherein close to at least a substantial fraction of all of the surface pores has at least one elevation extending over the implant surface which completely or at least partially surrounds an edge of said pore. Each elevation has a rough surface which causes formation of soft tissue when the implant surface is in contact with newly growing bone tissue, and thereby improves bond strength of the new grown bone tissue to the implant surface.

Generally, in order to achieve the desired retention improvement, at least one elevation around the pore should have a height of at least 1 $\mu$m, suitably at least 5 $\mu$m, over the surrounding material surface. The height is limited by conditions which have to do with production technology. The maximum height is typically not more than about 50 $\mu$m, and is usually in the region of about 20 $\mu$m, for example 1–15 $\mu$m.

The elevation(s) around the surface pores, according to the invention, can be produced according to various techniques. In those cases where the implant material, at least within the portion in question of the surface of the implant, consists of a material having a good ductility, such as most metals (also alloys are included in the concept of metals), the surface pores are suitably produced through thermal etching or through supersonic working. Depending on the curvature of the implant, supersonic working is generally preferred on comparatively flat regions, and thermal etching is typically used for more curved parts. For thermal etching, a laser is usually used, preferably of the YAG laser type or possibly of the carbon dioxide type. By proper arrangement of the apparatus, a desired geometry and pattern can be achieved, and by proper adjustment of the supplied power, the elevations around the pore edge can be created through crater formation at the establishment of the pore in those cases when the material is sufficiently ductile. Which materials are sufficiently ductile and how the pore formation is performed in order to create the crater formation and hence the desired elevations can be determined through empirical experiments.

If the material within the surface portion in question has poor ductility such that elevations such as craters cannot be formed upon formation of the pore by use a laser or the like (this is often the case for ceramics), the desired elevations around the pore instead can be formed by removing material in a region around the brim portion of the pore. In this way, the brim portion remains as an elevation higher than the surrounding surface.

When a joint is exposed to a shear force it will absorb energy by reversibly changing its shape up to a point, after which the joint fractures. If the joint is highly elastic, it will be able to store more energy by allowing a larger degree of displacement between the joint members. In the human body the joints between teeth and bone are composed of a large number of individual fibers connecting the two materials, which results in the joint exhibiting a semi-plastic behavior, despite the fibers being elastic. The reason for this semi-plastic behavior is that when a shear force is applied, the fibers are stretched, developing elastic behavior by reversible deformation of the fibers, as well as a displacement of the tooth in relation to its bone pocket. When the force is removed, the tooth reverts to its original position. If a stronger force is applied, the fibers will start breaking one by one, each behaving in an elastic member. When the force is removed, the tooth will revert to its original position, but this time with a weaker bonding, which is generally restored over time.

The inventor has discovered, in accordance with one aspect of the invention, that it is possible for the joint between a metallic implant, typically a titanium implant, to mimic to a considerable degree nature by the provision of surface pores having a proper size in combination with a proper pore brim topography. Importantly, it has been discovered that the provision of a rough brim or pore circumference area stimulates the formation of soft bonding tissue, which results in a significant increase in shear strength due to the resulting semi-plastic behavior. Typically, the pores are surrounded by a crater ridge having a height generally not higher than about 50μ.

The invention thus achieves an improved balance between retention and strength of the implant material. Through optimized ingrowth of bone tissue in surface pores having elevations according to the invention, the resistance against shear forces between implant and new grown bone can be increased from about 3–4 MPa for implants without surface pores and to more than about 8 MPa for implants having surface pores.

BRIEF DESCRIPTION OF DRAWINGS

In the following description, reference will be made to the accompanying drawings, in which.

DETAILED DESCRIPTION OF THE INVENTION

Figure 1:
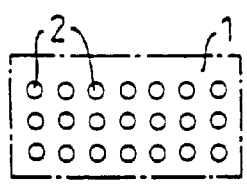
FIGS. 1A–C illustrate examples of some various patterns which the surface pores can form on the implant surface.

FIG. 1A shows a portion of an implant surface 1 having surface pores 2 arranged in a square pattern. FIG. 1B shows a portion of an implant surface 1 having surface pores 2 arranged in a hexagonal or rhombic pattern. FIG. 1C shows a portion of an implant surface 1 having surface pores 2 arranged in a spiral pattern.

Figure 2:
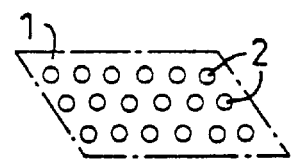
FIG. 2 shows some surface pores in FIG. 1A at a larger scale, FIG. 3 schematically shows a section through a surface pore along a line III—III in FIG. 2.
Figure 2:
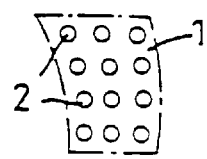
Figure 2:
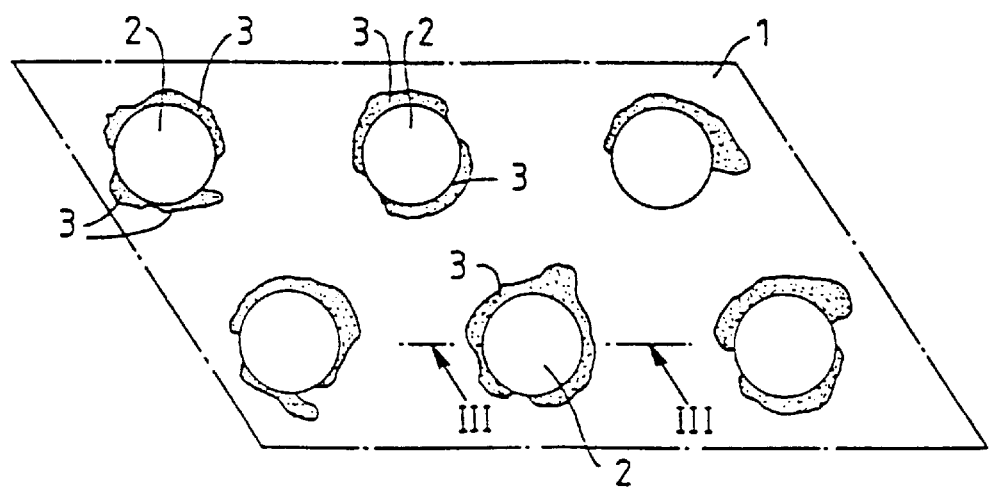

FIG. 2 shows a number of surface pores 2 having elevations 3 extending more or less continuously around the edge of the pore. The elevations 3 have the form of crater formations, which may arise at the formation of the surface pores through working by means of laser if such parameters as supplied power, time etc. are properly set.

Figure 3:
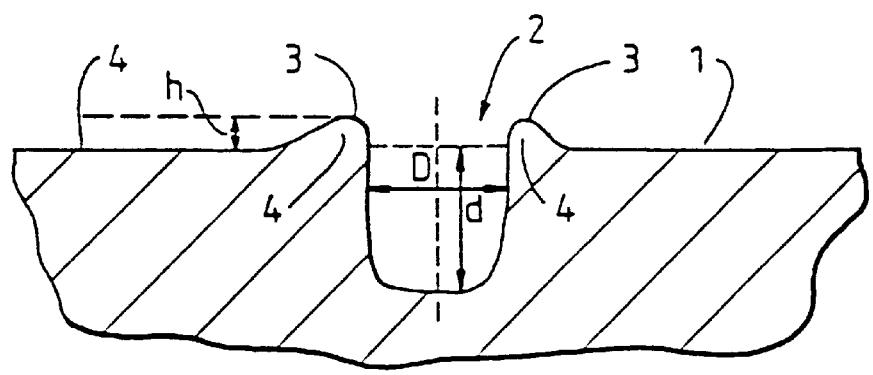

FIG. 3 illustrates how a pore 2 and the region adjacent to the pore may look in a typical case according to the invention. In the drawing, the diameter of the pore 2 is designated D and its depth is designated d. The maximal height of the elevation or elevations 3 over the material surface 4 surrounding the edge of the pore is designated h. The ratio between the diameter and the depth of the surface pores, D/d, and the height h of the elevation 3 are important for achieving improved retention. Thus D/d should be at least 0.5, for example 0.1–10, more usually in the range 0.5–2.

The mean diameter of the surface pores 2 lies between 100–200 μm, optimally between 125–180 μm. A suitable mean diameter is about 150 μm.

The surface pore depth is related to the diameter such that D/d is at least 0.5, typically not more than 10, for example 0.1–10, more usually in the range 0.5–2. The pore depth may be between 10–400 μm, for example 50–200 μm.

The height h under these conditions should be at least 1 μm, preferably at least 5 μm. The maximal height h is generally in the region of 20 μm.

The distance between adjacent surface pores should be between 50–200 μm. Typically, this distance is in the region of 75–150 μm.

Figure 4:
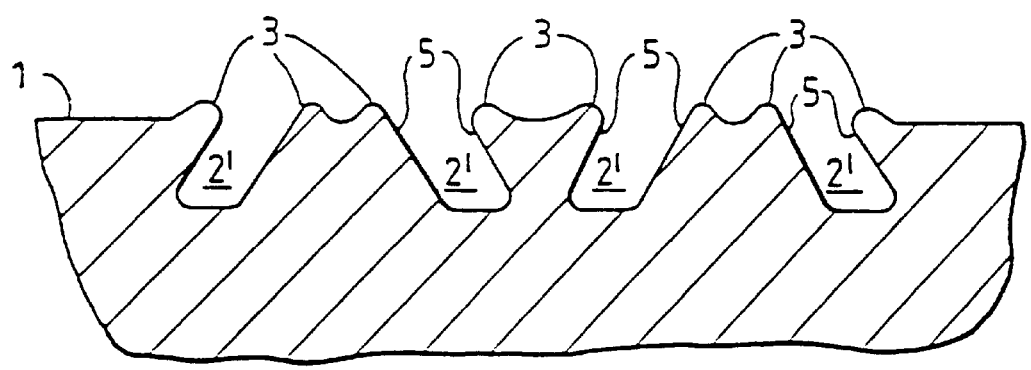
FIG. 4 shows a section through an embodiment having a theoretically ideal design with inclined surface pores.

FIG. 4 shows surface pores 2' having incline d pore walls 5, which in combination with the elevations 3 further enhances the retention. The inclination of the pore walls 5 may amount to about 30° relative to the normal directions of the surface pore openings.

Figure 5:
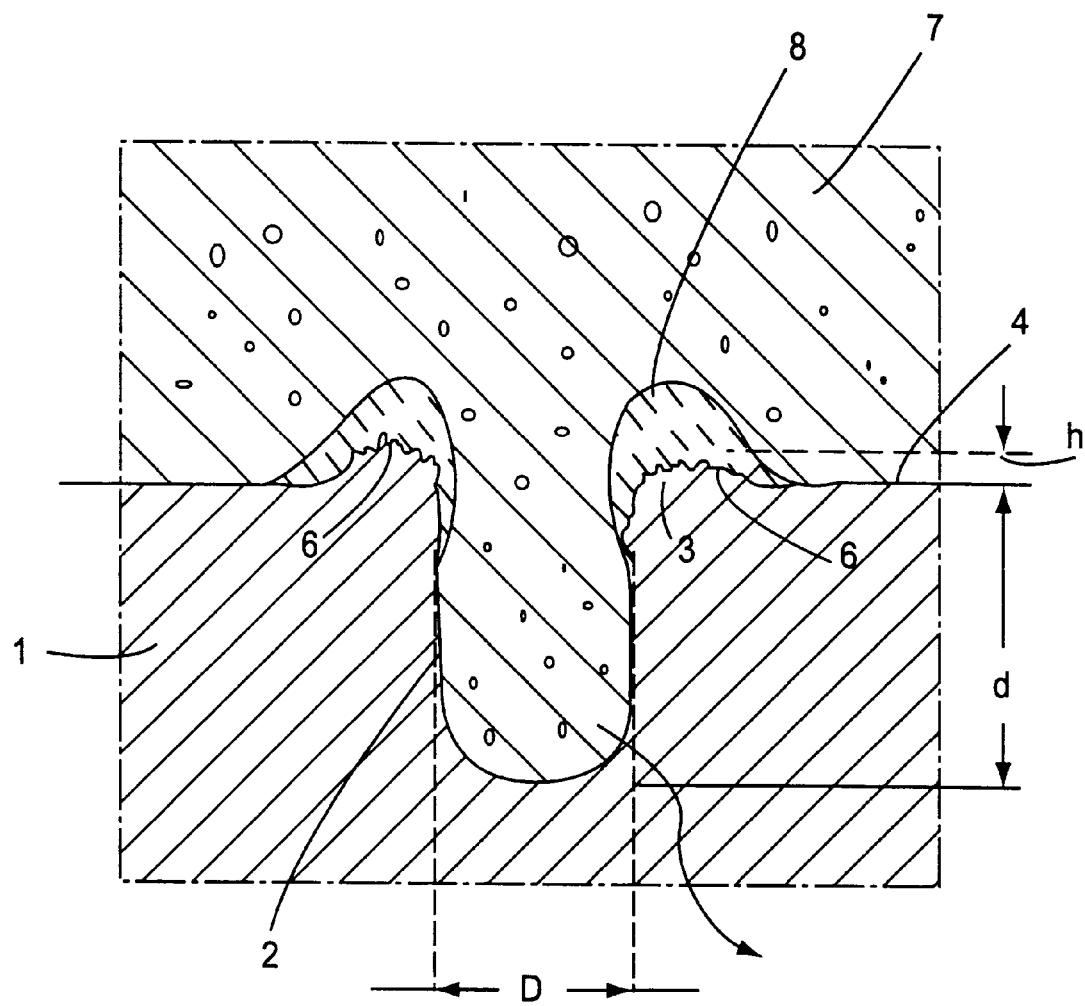
FIG. 5 shows an axial section through a surface pore with ingrown bone tissue in the pore and soft bonding tissue surrounding the pore.

FIG. 5 schematically illustrates an axial section through an implant 1 with an original implant surface 4, a surface pore 2 (diameter D; depth d) surrounded by elevations 3 having an unevenness shown as 6. Ingrown bone tissue 7 is in the pore and soft bonding tissue 8 surrounds the pore. The pores 2 irregularly surround the pore or parts of it in the brim area of the pore. The elevations resemble the shape of crater formations which may arise upon formation of the surface pores through working by means of laser if parameters such as supplied power, time, etc. are properly set. By applying only a single but very strong laser pulse, or a very few such pulses, material splashes out from the established pore, which promotes the irregular and desirable rough surface structure of the elevations. The pores may be made by a single laser pulse or by plural pulses up to a maximum of five to provide a significantly rough brim surface area and a moderate height of the elevations. Such rough elevations promote the formation of regions of soft bonding tissue 8.

It has been found according to the present invention that crater-like elevations surrounding the pores are important in order to improve the shear strength, but the elevations must not be so high that they form an obstacle for the desired ingrowth of bone tissue in the pores. Therefore, at least any elevation around the pore should have an altitude amounting to at least 1 μm, suitably at least 5 μm, over the surrounding material surface 4, but generally not exceeding a maximum height of about 50 μm, although a maximum height of about 20 μm may suffice for retention purposes. Another reason for controlling the height of the elevations is that the formation of high elevations around the pores requires repeated elimination of material during formation of the pores by laser operation. Such repeated laser operations tends to result in the material spreading out from the pore and accumulating as layers on top of each other, thereby reducing or eliminating roughness on the elevations, which is undesirable.

As use herein, the term "rough" or "roughness" when used in the context of the crater or elevation surfaces, means a surface which is sufficiently rough to cause the formation of soft tissue when the implant surface is in contact with the newly growing tissue. Typically, a rough surface is one where at least 1% of the crater ridge surface around at least some, suitably at least 10%, e.g. at least 50%, of the pores, shall be covered with small projections having a radius of at least 0.1 μm and not more than about 20 μm, and wherein the rough regions shall contain at least one such small projection per 100 μm². It may also be advantageous that there is no formation of soft issue around certain pores, in which case there will be obtained a combination of semi-plastic and more brittle properties, which may optimize the toughness of the mechanical bond between the implant surface and the newly grown bone tissue.

EXAMPLES

The invention will now be further illustrated by the following working examples.

Example 1

24 cylinders of a completely dense, i.e. without any pores interior of the surface, C P titanium having a diameter of 2.8 mm and a length of 6 mm were implanted in the femure of rabbits for 4 and 12 weeks, respectively. The rabbits were of type New Zealand White having a weight of about 4 kg. Half of the cylinders had pores, which were thermally etched by means of laser having the following apparatus parameters, wherein surface pores were achieved having a mean diameter of about 150 $\mu$m and a depth of the same order. Ridge shaped elevations were formed around the opening of the pores through the laser treatment, the ridges having a maximal height over the surrounding material surface of about 5 $\mu$m. The mean distance between the surface pores was about 120 $\mu$m.

Laser type YAG

The laser beam was moved to and fro over the cylinder surface in the axial direction, the cylinder being, turned between each change of movement direction.

Rate of movement: 630 mm/min

Turning angle appr 14°

Pulse frequency 30 Hz

Pulse width 0.13 ms

Lamp voltage 600 V

Pulse power 0.6 J

Beam path aperture 3.0 mm

Focal point 4.2 mm over the material surface

Prior to sterilization the implant samples were cleaned ultrasonically in HCl-solution for 1 h, whereafter the samples were stored in 1 M HCl-solution for 14 h. The samples finally were washed, first in de-ionized water and 70% alcohol and secondly in distilled water. The samples were sealed in special bags and autoclaved for 20 min. In the femure (a leg) of each rabbit three holes were drilled by means of a special drilling device at a distance of about 10 mm from each other and at a distance from the growth zone in cortical bone under a heavy saline flow in order to promote efficient cooling. A low drilling pressure was applied. The drilling produced holes having appr 0.1 mm play for the cylinder samples. After the period of implantation, the animals were put to death by an overdose of Mebumal, and were prepared for so called push-out tests and for histological evaluation.

A 10 mm long bone section with the implant in the center thereof was prepared from the femure. The bone sections were cut longitudinally in order to make available the part of the implant facing the bone marrow. The prepared bone was kept in 0.9% NaCl solution without any fixation. Bone with cylinder was placed in a push-out fixture by means of a dental cement. The maximal force required for loosening, the implant from the bone was detected by means of a universal instrument for measurement of strength (Alwetron) having a loading rate of 0.5 mm/min. The shear force between implant and bone was calculated through measured power divided by the present contact surface between bone and implant. The results are given in Table 1.

TABLE 1

Shear Power between Implant and Bone
(U = without surface pores   M = with surface pores)

| Animal No. | Implant 1 MPa 6 weeks | Implant 2 MPa 6 weeks | Implant 3 MPa 6 weeks | Animal No. | Implant 1 MPa 12 weeks | Implant 2 MPa 12 weeks | Implant 3 MPa 12 weeks |
|---|---|---|---|---|---|---|---|
| 1 | U 2.1 | M 8.3 | M 11.4 | 5 | U 3.7 | M 15.8 | M 17.2 |
| 2 | U 1.6 | M 7.9 | M 8.9 | 6 | U 4.3 | M 14.9 | M 20.1 |
| 3 | U 1.9 | U 2.3 | M 7.7 | 7 | U 3.3 | U 4.7 | M 18.8 |
| 4 | U 2.2 | U 0.8 | M 10.1 | 8 | U 4.2 | U 3.9 | M 16.4 |

Example 2

Figure 6:
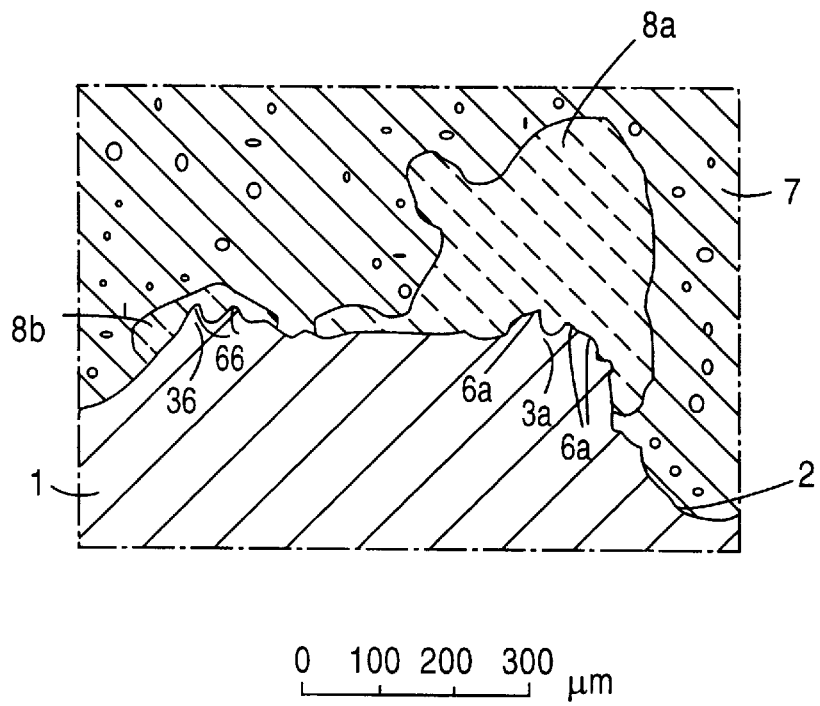
FIGS. 6 and 7 are drawings made from photomicrographs showing sections of a titanium implant of the invention.
Figure 7:
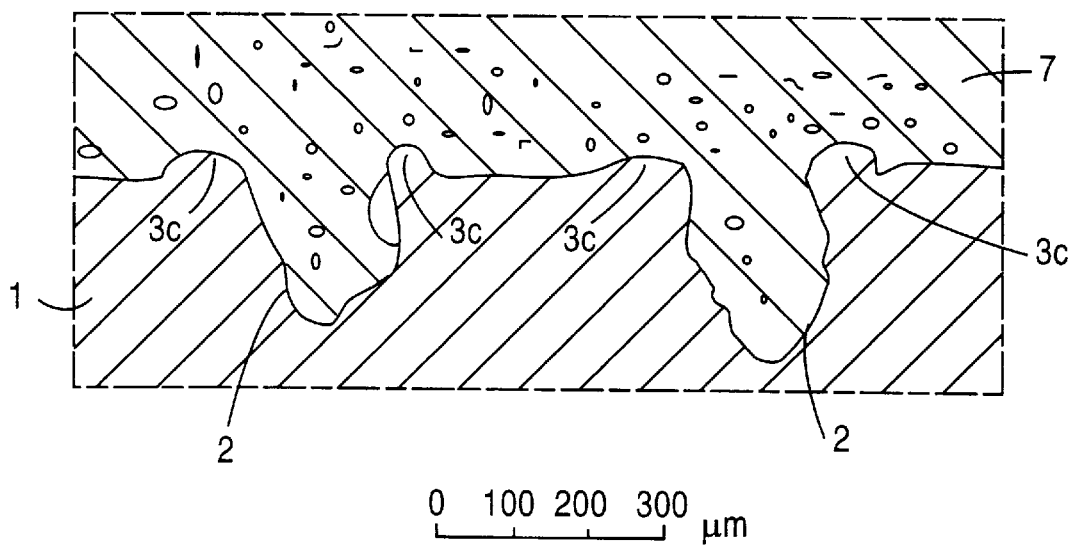

FIGS. 6 and 7 are drawings made from microphotographs showing sections of titanium implants 1 prepared as described in Example 1. The implants were implanted in holes in the femur of a rabbit. The photomicrographs show the ingrowth of bone after a period of time.

In FIG. 6, there is shown a pore 2 which is at least partly surrounded by a first crater 3a. A second crater 3b borders another pore (this is distorted in the drawing because the illustrated section does not coincide with and is not parallel with the axis of the pore). Both the craters 3a and 3b are very uneven. A plurality of projections or "knots" 6a are on the crater 3a. The overall height of the craters is in the region of about 20 $\mu$m. The radii of the knots 6a do not exceed 20 $\mu$m and are typically smaller than 5 $\mu$m. The minimum radius of a knot 6a is in the region of 0.1 $\mu$m. Typically, the majority of the craters 3a have a radius in the range 0.1 to 5 $\mu$m. The crater 3b has fewer projections or "knots" 6b, and the radii of the knots is less than 20 $\mu$m, typically in the region of or less than 5 $\mu$m, e.g. 0.1–5 $\mu$m.

In FIG. 6, new grown bone tissue 7 has grown into the pore 2. In the region of the rough craters 3a and 3b, however, there is a lack of direct bone-implant contact in the areas with sharp edges. Instead, soft tissue regions 8a and 8b have developed in those areas.

In contrast, FIG. 7 illustrates a titanium implant material 1 of the same type as the implant 1 of FIG. 7, which also has pores 2 and craters 3c, which have an overall height of about 30 $\mu$m. They are, however, comparatively smooth. While the new-grown bone tissue has reached the bottom of the pores 2, there has not been developed any soft tissue around the pores. It is believed that this is due to the fact that the craters 3c are substantially even on their surfaces, in contrast to the rough craters 3a and 3b. It is also to be noted that the size of the soft tissue regions varies depending on the degree of roughness. Thus, a large soft tissue region 8a has covered the crater 3a, where the formation of "knots" is very dense, whereas the soft tissue region 8b, which covers the less rough crater 3b, which has only a few "knots", is much smaller.

Example 3

In order to evaluate the importance of the pore diameters, titanium implants were prepared with different pore sizes. The implants were of the same type and sizes and were prepared as previously described in Example 1, and then implanted in the femur of the rabbit. The control implant specimen had no pores.

Figure 8:
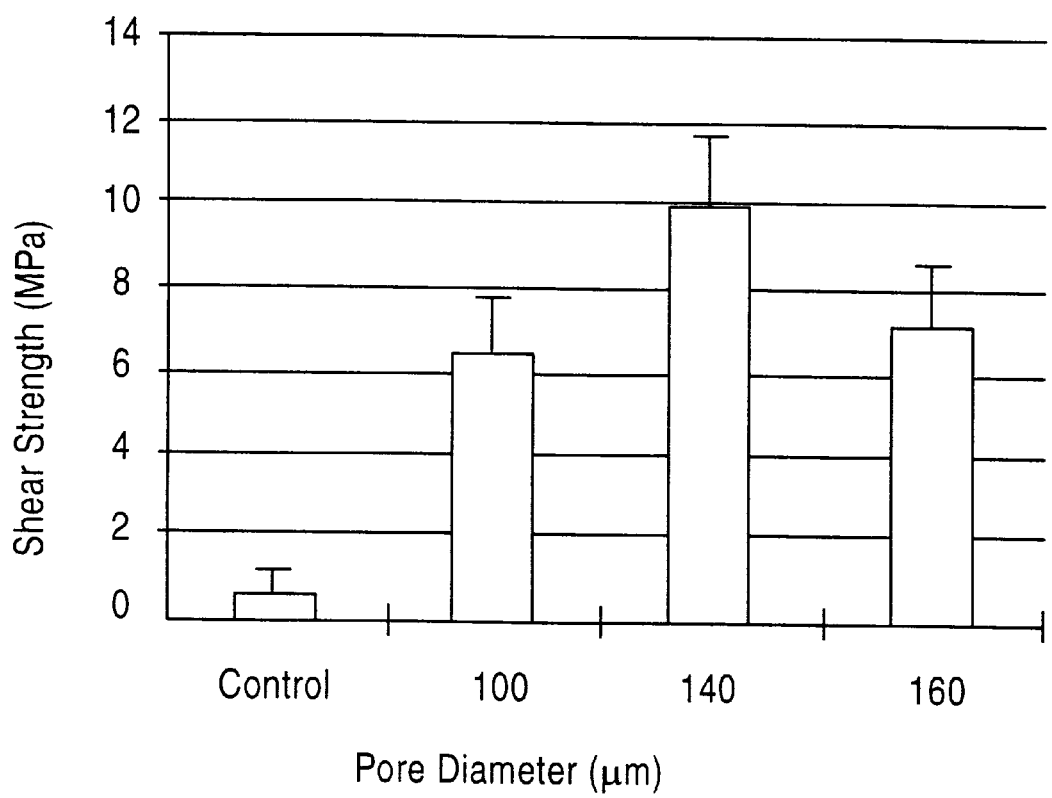
FIG. 8 shows the shear strength (MPa) as a function of pore diameter.

FIG. 8 shows the shear strength, MPa, six weeks after implantation. Shear strength of the implants with pores are significantly higher than the control group without pores.

Among the implants with pores, those with 140 μm diameter pores had the highest shear strength. The experiment demonstrates that good results in terms of shear strength are observed if the pore diameters are greater than 100 μm and smaller than 200 μm, with an optimum between 125 and 180 μm. The optimum pore size appears to be of the order of 150 μm.

We claim:

1. An implant intended to be fixed through contact with new grown bone tissue, said implant comprising a dense material having an implant surface and having, at least within a surface portion of said implant surface, surface pores covering at least 5% of said surface portion, said surface pores constituting a contact surface for new grown bone tissue, wherein at least a substantial fraction of all of said surface pores has at least one elevation extending over said implant surface which completely or at least partially surrounds an edge of said pore, said at least one elevation having a rough surface which causes formation of soft tissue when the implant surface is in contact with newly growing bone tissue, said rough surface being such that at least 1% of the elevation surface around at least 10% of the pores is covered with projections having a radius of at least 0.1 μm and not more than about 20 μm.

2. An implant according to claim 1, wherein said at least one elevation has a maximal height over said implant surface of at least one μm.

3. An implant according to claim 2, wherein said maximal height is not more than about 50 μm.

4. An implant according to claim 1, wherein said rough surfaces contain at least one small projection per 100 μm².

5. An implant according to claim 1, wherein said implant surface comprising said surface portion having said surface pores consists of titanium.

6. An implant intended to be fixed through contact with new grown bone tissue, said implant comprising a dense material having an implant surface and having, at least within a surface portion of said implant surface, surface pores covering at least 5% of said surface portion, said surface pores constituting a contact surface for new grown bone tissue, at least a substantial fraction of all of said surface pores has at least one elevation which is higher than said implant surface and which completely or at least partially surrounds an edge of said pore, said at least one elevation having a maximal height over said implant surface of at least 1 μm, said surface pores having a mean diameter of between 100 and 200 μm, said surface pores having a depth of between 50 and 200 μm, and wherein adjacent pores are separated by a distance of between 50 and 200 μm, said at least one elevation having a rough surface which causes formation of soft bone tissue when the implant surface is in contact with newly growing bone tissue, said rough surface being such that at least 1% of the elevation surface around at least 10% of the pores is covered with projections having a radius of at least 0.1 μm and not more than about 20 μm.

7. An implant according to claim 6, wherein said maximal height of said at least one elevation over said implant surface is at least 5 μm.

8. An implant according to claim 6, wherein said maximal height of said at least one elevation over said implant surface is not more than about 20 μm.

9. An implant according to claim 6, wherein said pores have a diameter D and a depth d, with D/d being at least 0.5.

10. An implant according to claim 9, wherein D/d is 0.1–10.

11. An implant according to claim 6, wherein said implant surface comprising said surface portion having said surface pores is comprised of a material selected from the group consisting of a metal, a polymer and a composite material consisting substantially of a metal or a polymer.

12. An implant according to claim 6, wherein said implant surface comprising said surface portion having said surface pores is comprised of a material selected from the group consisting of a ceramic and a composite material consisting essentially of a ceramic material.

13. An implant according to claim 6, wherein said surface pores as well as said at least one elevation which completely or partly surrounds said surface pores are produced by way of a laser treatment of said material.

14. An implant according to claim 6, wherein said implant surface comprising said surface portion having said surface pores consists of titanium.

* * * * *